United States Patent
Röben et al.

(10) Patent No.: US 9,388,201 B2
(45) Date of Patent: Jul. 12, 2016

(54) UREA-CONTAINING SILANES, PROCESS FOR PREPARATION THEREOF AND USE THEREOF

(71) Applicant: Evonik Industries AG, Essen (DE)

(72) Inventors: Caren Röben, Köln (DE); Ralph Moser, Freiburg i. Br. (DE); Stefanie Mayer, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/711,463

(22) Filed: May 13, 2015

(65) Prior Publication Data
US 2015/0329571 A1    Nov. 19, 2015

(30) Foreign Application Priority Data

May 15, 2014 (DE) .......................... 10 2014 209 239

(51) Int. Cl.
| | | |
|---|---|---|
| *C07F 7/10* | (2006.01) | |
| *C07F 7/18* | (2006.01) | |
| *C08C 19/25* | (2006.01) | |
| *C08G 77/00* | (2006.01) | |
| *C08L 83/00* | (2006.01) | |
| *C08L 9/06* | (2006.01) | |

(52) U.S. Cl.
CPC .............. *C07F 7/1836* (2013.01); *C07F 7/1892* (2013.01); *C08C 19/25* (2013.01); *C08G 77/00* (2013.01); *C08L 9/06* (2013.01); *C08L 83/00* (2013.01)

(58) Field of Classification Search
CPC ................................ C07F 7/18; C07F 7/1836
USPC .......................................................... 556/421
See application file for complete search history.

(56) References Cited

U.S. PATENT DOCUMENTS

| | | | |
|---|---|---|---|
| 2,509,483 | A | 5/1950 | Crouch |
| 3,637,789 | A | 1/1972 | Legendre |
| 3,946,059 | A | 3/1976 | Janssen et al. |
| 6,375,789 | B1 | 4/2002 | Katz et al. |
| 2003/0191270 | A1 | 10/2003 | Musa |
| 2009/0075096 | A1 | 3/2009 | Butikofer |

FOREIGN PATENT DOCUMENTS

| | | |
|---|---|---|
| DE | 3424534 | 1/1986 |
| DE | 10351735 | 12/2004 |
| DE | 60018483 | 1/2006 |
| EP | 1156053 | 11/2001 |
| EP | 1700861 | 9/2006 |
| EP | 2570419 | 3/2013 |
| JP | S59144792 | 8/1984 |
| JP | 2002201312 | 7/2002 |

(Continued)

OTHER PUBLICATIONS

Besson et al., Journal of Materials Chemistry (2009), 19(27), 4746-4752.*

(Continued)

*Primary Examiner* — Porfirio Nazario Gonzalez
*Assistant Examiner* — Kofi Adzamli
(74) *Attorney, Agent, or Firm* — Michael Best & Friedrich LLP

(57) ABSTRACT

The invention relates to urea-containing silanes of the formula I

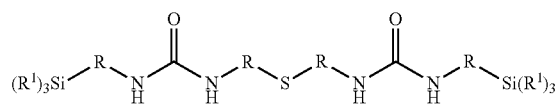

which are prepared by, in a first step, reacting an aminosilane of the formula II

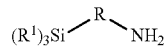

with an isocyanate of the formula III

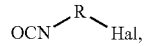

and, in a second step, reacting the product from the first process step with sodium sulphide of the formula IV Na₂S    (IV)

or in a first step, reacting an isocyanatosilane of the formula VI

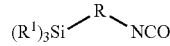

with an amine of the formula VII

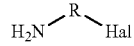

and, in a second step, reacting the product from the first process step with sodium sulphide of the formula IV Na₂S    (IV).

16 Claims, No Drawings

(56) References Cited

FOREIGN PATENT DOCUMENTS

| JP | 2002311574 | 10/2002 |
|----|------------|---------|
| JP | 2008279736 | 11/2008 |
| WO | 99/55754 | 11/1999 |
| WO | 2013/087698 | 6/2013 |

OTHER PUBLICATIONS

Wang et al., Database Accession No. 2014:1102076 (2014).

German Search Report for Application No. 15165590.9 dated Oct. 23, 2015 (9 pages).

Besson et al., "Soft route for monodisperse gold nanoparticles confined within SH-functionalized walls of mesoporous silica," J. Mat. Chem., 2009, 19, pp. 4746-4752.

German Search report for Application No. 102014209215.9 dated Jul. 31, 2014 (6 pages).

German Search report for Application No. 102014209221.3 dated Jul. 31, 2014 (5 pages).

German Search Report for Application No. 102014209226.4 dated Aug. 5, 2014 (6 pages).

German Search Report for Application No. 102014209239.6 dated Oct. 8, 2014 (6 pages).

Harpp et al., "Organic Sulfur Chemistry. X. Selective Desulfurization of Disulfides. Scope and Mechanism," Organic Sulfur Chemistry, 1970, pp. 2437-2443.

Wang et al, "Fabrication of Single-Hole Glutathione-Responsive Degradable Hollow Silica Nanoparticles for Drug Delivery," Applied Materials and Interfaces, American Chemical Society, 2014, 6, pp. 12600-12608.

United States Patent Office Notice of Allowance for U.S. Appl. No. 14/711,478 dated Jul. 17, 2015 (8 pages).

German Search Report for Application No. 102014209233.7 dated Oct. 13, 2014 (6 pages).

European Patent Office Search Report for Application No. 15165635.2 dated Sep. 17, 2015 (3 pages).

European Patent Office Search Report for Application No. 15161560.6 dated Oct. 7, 2015 (6 pages).

European Patent Office Search Report for Application No. 15161573.9 dated Oct. 2, 2015 (7 pages).

European Patent Office Search Report for Application No. 15161605.9 dated Oct. 6, 2015 (8 pages).

Xu et al., "A new strategy to prepare glutathione responsive silica nanoparticles," RSC Advances, 2013, 3, p. 17700.

Gudima, N.V. et al., "Sorption of gold and palladium on silica gel modified by N-(4-mercaptophenyl)-N'-propylurea groups," Ukrainskii Khimicheskii Zhurnal (Russian Edition), 2010, 76, pp. 114-118.

Mane et al., "An efficient and greener protocol towards synthesis of unsymetrical N,N'-biphenyl urea," Arabian Journal of Chemistry, 2011, 6, pp. 423-427.

United States Patent Office Notice of Allowance for U.S. Appl. No. 14/711,478 dated Sep. 25, 2015 (5 pages).

United States Patent Office Notice of Allowance for U.S. Appl. No. 14/711,468 dated May 13, 2016 (12 pages).

United States Patent Office Action for U.S. Appl. No. 14/711,473 dated May 11, 2016 (8 pages).

United States Patent Office Notice of Allowance for U.S. Appl. No. 14/711,486 dated Mar. 11, 2016 (10 pages0.

\* cited by examiner

UREA-CONTAINING SILANES, PROCESS FOR PREPARATION THEREOF AND USE THEREOF

CROSS-REFERENCE TO RELATED APPLICATIONS

This patent application claims the benefit of priority to German Application No. 102014209239.6, filed on May 15, 2014, the disclosure of which is incorporated by reference herein in its entirety, and priority to which is hereby claimed.

The invention relates to urea-containing silanes, to processes for preparation thereof and to the use thereof.

CAS 1184961-62-3, 442527-46-0 and 498553-03-0 disclose compounds of the formula

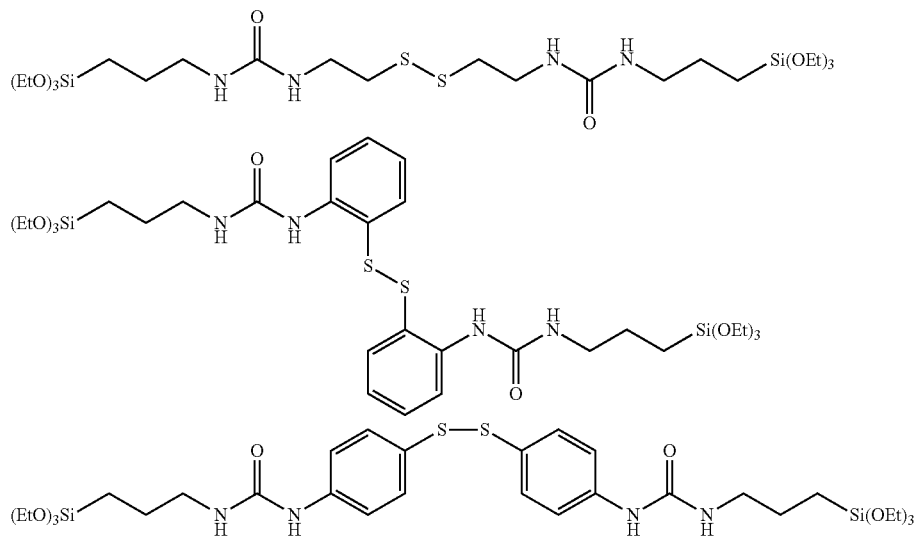

In addition, US 20030191270 A1 discloses silanes of the formula

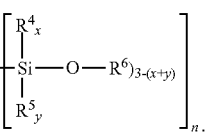

JP 2002201312 A discloses rubber modifiers of the formula

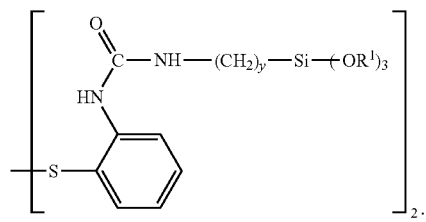

In addition, J. Mat. Chem. 2009, 19, 4746-4752 discloses gold nanoparticles within SH-functionalized framework structures formed from mesoporous silicas and the preparation of urea-containing silanes. In the known process, organic solvents are used.

Disadvantages of the known urea-containing disulphide silanes are poor processing characteristics, poor wet skid characteristics and low dynamic viscosity.

It is an object of the present invention to provide urea-containing silanes having improved processing characteristics, wet skid characteristics and dynamic viscosity in rubber mixtures compared to urea-containing silanes known from the prior art.

The invention provides a urea-containing silane of the formula I

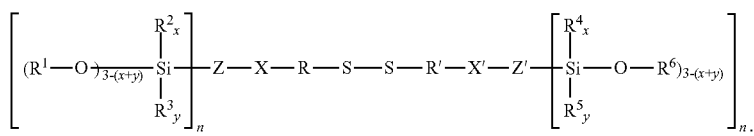

(I)

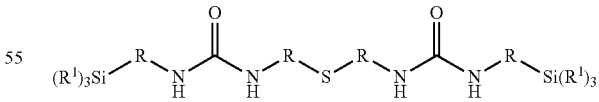

where $R^1$ are the same or different and are C1-C10 alkoxy groups, preferably methoxy or ethoxy group, C2-C10 cyclic dialkoxy groups, phenoxy group, C4-C10 cycloalkoxy groups, C6-C20 aryl groups, preferably phenyl, C1-C10 alkyl groups, preferably methyl or ethyl, C2-C20 alkenyl group, C7-C20 aralkyl group or halogen, preferably Cl, and R are the same or different and are a branched or unbranched, saturated or unsaturated, aliphatic, aromatic or mixed aliphatic/aromatic divalent C1-C30, preferably C1-C20, more preferably C1-C10, even more preferably C1-07, especially preferably C2 and C3, hydrocarbon group optionally substituted by F—, Cl—, Br—, I—, —CN or HS—.

Urea-containing silanes may be mixtures of urea-containing silanes of the formula I.

The process product may comprise oligomers which form through hydrolysis and condensation of the alkoxysilane functions of the urea-containing silanes of the formula I.

The urea-containing silanes of the formula I may be applied to a support, for example wax, polymer or carbon black. The urea-containing silanes of the formula I may be applied to a silica, in which case the binding may be physical or chemical.

R may preferably be:
—CH$_2$—, —CH$_2$CH$_2$—, —CH$_2$CH$_2$CH$_2$—, —CH$_2$CH$_2$CH$_2$CH$_2$—, —CH(CH$_3$)—, —CH$_2$CH(CH$_3$)—, —CH(CH$_3$) CH$_2$—, —C(CH$_3$)$_2$—, —CH(C$_2$H$_5$)—, —CH$_2$CH$_2$CH(CH$_3$)—, —CH(CH$_3$)CH$_2$CH$_2$—, —CH$_2$CH(CH$_3$)CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$CH$_2$— or

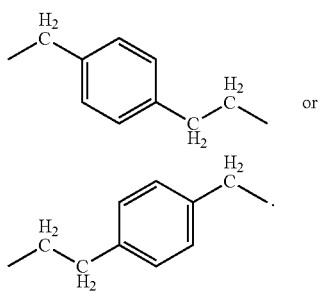

$R^1$ may preferably be methoxy or ethoxy.

Urea-containing silanes of the formula I may preferably be:
((EtO)$_3$Si—CH$_2$—NH—CO—NH—CH$_2$)$_2$S,
((EtO)$_3$Si—CH$_2$CH$_2$—NH—CO—NH—CH$_2$)$_2$S,
((EtO)$_3$Si—CH$_2$—NH—CO—NH—CH$_2$CH$_2$)$_2$S,
((EtO)$_3$Si—CH$_2$CH$_2$—NH—CO—NH—CH$_2$CH$_2$)$_2$S,
((EtO)$_3$Si—CH$_2$CH$_2$CH$_2$—NH—CO—NH—CH$_2$)$_2$S,
((EtO)$_3$Si—CH$_2$CH$_2$CH$_2$—NH—CO—NH—CH$_2$CH$_2$)$_2$S,
((EtO)$_3$Si—CH$_2$—NH—CO—NH—CH$_2$CH$_2$CH$_2$)$_2$S,
((EtO)$_3$Si—CH$_2$CH$_2$—NH—CO—NH—CH$_2$CH$_2$CH$_2$)$_2$S,
((EtO)$_3$Si—CH$_2$CH$_2$CH$_2$—NH—CO—NH—CH$_2$CH$_2$CH$_2$)$_2$S,
((MeO)$_3$Si—CH$_2$—NH—CO—NH—CH$_2$)$_2$S,
((MeO)$_3$Si—CH$_2$CH$_2$—NH—CO—NH—CH$_2$)$_2$S,
((MeO)$_3$Si—CH$_2$—NH—CO—NH—CH$_2$CH$_2$)$_2$S,
((MeO)$_3$Si—CH$_2$CH$_2$—NH—CO—NH—CH$_2$CH$_2$)$_2$S,
((MeO)$_3$Si—CH$_2$CH$_2$CH$_2$—NH—CO—NH—CH$_2$)$_2$S,
((MeO)$_3$Si—CH$_2$CH$_2$CH$_2$—NH—CO—NH—CH$_2$CH$_2$)$_2$S,
((MeO)$_3$Si—CH$_2$—NH—CO—NH—CH$_2$CH$_2$CH$_2$)$_2$S,
((MeO)$_3$Si—CH$_2$CH$_2$—NH—CO—NH—CH$_2$CH$_2$CH$_2$)$_2$S or
((MeO)$_3$Si—CH$_2$CH$_2$CH$_2$—NH—CO—NH—CH$_2$CH$_2$CH$_2$)$_2$S.

An especially preferred compound is of the formula
(EtO)$_3$Si—CH$_2$CH$_2$CH$_2$—NH—CO—NH—CH$_2$CH$_2$—S—CH$_2$CH$_2$—NH—CO—NH—CH$_2$CH$_2$CH$_2$—Si(OEt)$_3$.

The invention further provides a first process for preparing the inventive urea-containing silanes of the formula I

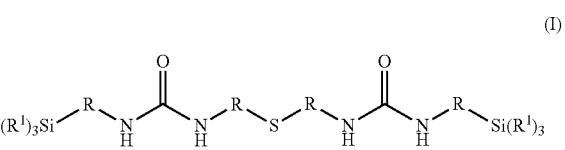

where $R^1$ and R are each as defined above, which is characterized in that, in a first step, an aminosilane of the formula II

is reacted with an isocyanate of the formula III

where R and $R^1$ are each as defined above and Hal is F, Cl, Br or I, preferably Cl, and, in a second step, the product from the first process step is reacted with sodium sulphide of the formula (IV)

Compounds of the formula II may preferably be:
(C$_2$H$_5$O)$_3$Si—CH$_2$—NH$_2$,
(C$_2$H$_5$O)$_3$Si—CH$_2$CH$_2$—NH$_2$,
(C$_2$H$_5$O)$_3$Si—CH$_2$CH$_2$CH$_2$—NH$_2$,
(CH$_3$O)$_3$Si—CH$_2$—NH$_2$,
(CH$_3$O)$_3$Si—CH$_2$CH$_2$—NH$_2$ or
(CH$_3$O)$_3$Si—CH$_2$CH$_2$CH$_2$—NH$_2$.

Compounds of the formula III may preferably be:
OCN—CH$_2$—Cl
OCN—CH$_2$CH$_2$—Cl or
OCN—CH$_2$CH$_2$CH$_2$—Cl, In the first process according to the invention, the first and second process step can be effected in one reaction vessel by addition of all the reactants.

In the first step of the first process according to the invention, the aminosilane of the formula II can be metered into isocyanate of the formula III.

In the first step of the first process according to the invention, the isocyanate of the formula III can preferably be metered into aminosilane of the formula II.

In the first step of the first process according to the invention, the aminosilanes of the formula II can be used relative to isocyanates of the formula III in a molar ratio of 0.85:1 to 1.15:1, preferably 0.90:1 to 1.10:1, more preferably in a ratio of 0.95:1 to 1.05:1.

The reaction in the first step of the first process according to the invention can be conducted with exclusion of air.

The reaction in the first step of the first process according to the invention can be conducted under a protective gas atmosphere, for example under argon or nitrogen, preferably under nitrogen.

The first step of the first process according to the invention can be conducted at standard pressure, elevated pressure or reduced pressure. Preferably, the process according to the invention can be conducted at standard pressure.

Elevated pressure may be a pressure from 1.1 bar to 100 bar, preferably of 1.5 bar to 50 bar, more preferably of 2 bar to 20 bar and very preferably of 2 to 10 bar.

Reduced pressure may be a pressure of 1 mbar to 1000 mbar, preferably 1 mbar to 500 mbar, more preferably 1 mbar to 250 mbar, very preferably 5 mbar to 100 mbar.

The first step of the first process according to the invention can be conducted between −78° C. and 100° C., preferably between −70° C. and 50° C., more preferably between −65° C. and 25° C.

The reaction in the first step of the first process according to the invention can be effected without solvent or in a solvent, for example methanol, ethanol, propanol, butanol, cyclohexanol, N,N-dimethylformamide, dimethyl sulphoxide, pentane, hexane, cyclohexane, heptane, octane, decane, toluene, xylene, acetone, acetonitrile, carbon tetrachloride, chloroform, dichloromethane, 1,2-dichloromethane, tetrachloroethylene, diethyl ether, methyl tert-butyl ether, methyl ethyl ketone, tetrahydrofuran, dioxane, pyridine or ethyl acetate. The solvent may preferably be dichloromethane, ethanol, methyl tert-butyl ether, toluene, ethyl acetate, pentane or hexane.

The reaction in the first step of the first process according to the invention can be conducted without organic solvent. The solvent may be water.

The solvent in the first step of the first process according to the invention can subsequently be removed, preferably distilled off.

The reaction product in the first step of the first process according to the invention can subsequently be filtered and washed with an organic solvent. Preferably, an alkane can be used for washing, more preferably hexane.

The reaction product in the first step of the first process according to the invention can be dried after filtration. The drying can be effected at temperatures of 20° C.-100° C., preferably of 25° C.-50° C. The drying can be effected at a reduced pressure of 1-500 mbar.

The urea-containing halosilane of the formula V, obtainable in the first step of the first process according to the invention,

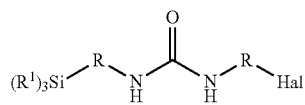

(V)

can be obtained in a yield of greater than 50%, preferably greater than 60%, very preferably greater than 70%.

The reaction in the second step of the first process according to the invention can be conducted with exclusion of air.

The reaction in the second step of the first process according to the invention can be conducted under a protective gas atmosphere, for example under argon or nitrogen, preferably under nitrogen.

The second step of the first process according to the invention can be conducted at standard pressure, elevated pressure or reduced pressure. Preferably, the process according to the invention can be conducted at standard pressure.

Elevated pressure may be a pressure from 1.1 bar to 100 bar, preferably of 1.5 bar to 50 bar, more preferably of 2 bar to 20 bar and very preferably of 2 to 10 bar.

Reduced pressure may be a pressure of 1 mbar to 1000 mbar, preferably 1 mbar to 500 mbar, more preferably 1 mbar to 250 mbar, very preferably 5 mbar to 100 mbar.

The second step of the first process according to the invention can be conducted between 20° C. and 150° C., preferably between 40° C. and 100° C., more preferably between 45° C. and 80° C.

The reaction in the second step of the first process according to the invention can be effected without solvent or in a solvent, for example methanol, ethanol, propanol, butanol, cyclohexanol, N,N-dimethylformamide, dimethyl sulphoxide, pentane, hexane, cyclohexane, heptane, octane, decane, toluene, xylene, acetone, acetonitrile, carbon tetrachloride, chloroform, dichloromethane, 1,2-dichloromethane, tetrachloroethylene, diethyl ether, methyl tert-butyl ether, methyl ethyl ketone, tetrahydrofuran, dioxane, pyridine or ethyl acetate. The solvent may preferably be ethanol.

The reaction in the second step of the first process according to the invention can be conducted without organic solvent. The solvent may be water.

The reaction product in the second step of the first process according to the invention can be filtered, and the filtercake can be washed with an organic solvent. Preferably, an alcohol can be used for washing, more preferably ethanol, or an alkane, more preferably hexane.

The solvent in the second step of the first process according to the invention can subsequently be removed, preferably distilled off.

The reaction product in the second step of the first process according to the invention can be dried after filtration and removal of solvent. The drying can be effected at temperatures of 20° C.-100° C., preferably of 25° C.-50° C. The drying can be effected at a reduced pressure of 1-500 mbar.

The urea-containing silane of the formula I, obtainable in the second step of the first process according to the invention,

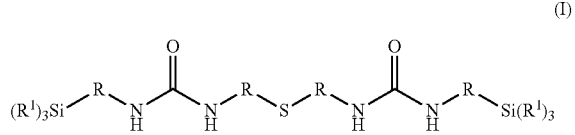

(I)

can be obtained in a yield of greater than 50%, preferably greater than 60%, very preferably greater than 70%.

The product prepared by the first process according to the invention may have a residual content of urea-containing halosilane of the formula V of less than 25 mol %, preferably less than 10 mol %, more preferably less than 5 mol %, very preferably less than 3 mol %.

The relative molar percentages of the urea-containing halosilanes of the formula V in the product prepared by the first process according to the invention are determined in the $^1$H NMR by integration of the hydrogen atoms in the —CH$_2$CH$_2$—Cl group of the urea-containing halosilanes of the formula V against the hydrogen atoms in the Si—CH$_2$— group of the urea-containing silanes of the formula I.

For the substance of the formula V (EtO)$_3$Si—CH$_2$CH$_2$CH$_2$—NH—CO—NH—CH$_2$CH$_2$—Cl, for example, the integral of the hydrogen atoms of the —CH$_2$CH$_2$—Cl group (δ=3.17 ppm) is used for the determination of the relative contents.

The product prepared by the first process according to the invention may have a residual content of aminosilane of the formula II of less than 10 mol %, preferably less than 5 mol %, more preferably less than 1 mol %, very preferably less than 0.1 mol %.

The relative molar percentages of the aminosilanes of the formula II in the product prepared by the first process according to the invention are determined in the $^{13}$C NMR by integration of the carbon atoms in the —CH$_2$—NH$_2$ group of the aminosilanes of the formula II against the carbon atoms in the Si—CH$_2$— group of the urea-containing silanes of the formula I.

For the substance of the formula II (EtO)$_3$Si—CH$_2$—CH$_2$—CH$_2$—NH$_2$, for example, the integral of the carbon atoms of the —CH$_2$—NH$_2$ group (δ=45.15 ppm) is used for the determination of the relative contents.

The product prepared by the first process according to the invention may have a residual content of isocyanate of the formula III of less than 25 mol %, preferably less than 10 mol %, more preferably less than 5 mol %, very preferably less than 3 mol %.

The relative molar percentages of the isocyanates of the formula III in the product prepared by the first process according to the invention are determined in the $^{13}$C NMR by integration of the carbon atoms in the OCN—CH$_2$— group of the isocyanates of the formula III against the carbon atoms in the Si—CH$_2$— group of the urea-containing silanes of the formula I.

For the substance of the formula III OCN—CH$_2$—CH$_2$—Cl, for example, the integral of the carbon atoms of the OCN—CH$_2$— group (δ=124.33 ppm) is used for the determination of the relative contents.

The invention further provides a second process for preparing the inventive urea-containing silanes of the formula I

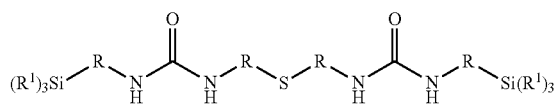
(I)

where R$^1$ and R are each as defined above, which is characterized in that, in a first step, an isocyanatosilane of the formula VI

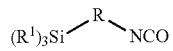
(VI)

is reacted with an amine of the formula VII

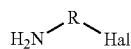
(VII)

where R and R$^1$ are each as defined above and Hal is F, Cl, Br or I, preferably Cl, and, in a second step, the product from the first process step is reacted with sodium sulphide of the formula IV

(IV).

Compounds of the formula VI may preferably be:
(C$_2$H$_5$O)$_3$Si—CH$_2$—NCO,
(C$_2$H$_5$O)$_3$Si—CH$_2$CH$_2$—NCO,
(C$_2$H$_5$O)$_3$Si—CH$_2$CH$_2$CH$_2$—NCO,
(CH$_3$O)$_3$Si—CH$_2$—NCO,
(CH$_3$O)$_3$Si—CH$_2$CH$_2$—NCO or
(CH$_3$O)$_3$Si—CH$_2$CH$_2$CH$_2$—NCO.

Compounds of the formula VII may preferably be:
H$_2$N—CH$_2$—Cl,
H$_2$N—CH$_2$CH$_2$—Cl or
H$_2$N—CH$_2$CH$_2$CH$_2$—Cl.

In the second process according to the invention, the first and second process step can be effected in one reaction vessel by addition of all the reactants.

In the first step of the second process according to the invention, amines of the formula VII can be metered into isocyanatosilanes of the formula VI.

In the first step of the second process according to the invention, the isocyanatosilanes of the formula VI can preferably be metered into amines of the formula VII.

In the first step of the second process according to the invention, the isocyanatosilanes of the formula VI can be used relative to amines of the formula VII in a molar ratio of 0.85:1 to 1.15:1, preferably 0.90:1 to 1.10:1, more preferably in a ratio of 0.95:1 to 1.05:1.

The reaction in the first step of the second process according to the invention can be conducted with exclusion of air.

The reaction in the first step of the second process according to the invention can be conducted under a protective gas atmosphere, for example under argon or nitrogen, preferably under nitrogen.

The first step of the second process according to the invention can be conducted at standard pressure, elevated pressure or reduced pressure. Preferably, the process according to the invention can be conducted at standard pressure.

Elevated pressure may be a pressure from 1.1 bar to 100 bar, preferably of 1.5 bar to 50 bar, more preferably of 2 bar to 20 bar and very preferably of 2 to 10 bar.

Reduced pressure may be a pressure of 1 mbar to 1000 mbar, preferably 1 mbar to 500 mbar, more preferably 1 mbar to 250 mbar, very preferably 5 mbar to 100 mbar.

The first step of the second process according to the invention can be conducted between −78° C. and 100° C., preferably between −75° C. and 60° C., more preferably between −70° C. and 40° C.

The reaction in the first step can be effected without solvent or in a solvent, for example methanol, ethanol, propanol, butanol, cyclohexanol, N,N-dimethylformamide, dimethyl sulphoxide, pentane, hexane, cyclohexane, heptane, octane, decane, toluene, xylene, acetone, acetonitrile, carbon tetrachloride, chloroform, dichloromethane, 1,2-dichloromethane, tetrachloroethylene, diethyl ether, methyl tert-butyl ether, methyl ethyl ketone, tetrahydrofuran, dioxane, pyridine or ethyl acetate.

The reaction in the first step of the second process according to the invention can be conducted without organic solvent. The solvent may preferably be water.

The solvent in the first step of the second process according to the invention can subsequently be removed, preferably distilled off.

The reaction product in the first step of the second process according to the invention can subsequently be filtered and washed with an organic solvent. Preferably, an alkane can be used for washing, more preferably hexane.

The reaction product in the first step of the second process according to the invention can be dried after filtration. The drying can be effected at temperatures of 20° C.-100° C., preferably of 25° C.-50° C. The drying can be effected at a reduced pressure of 1-500 mbar.

The urea-containing halosilane of the formula V, obtainable in the first step of the second process according to the invention,

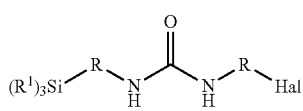

(V)

can be obtained in a yield of greater than 50%, preferably greater than 60%, very preferably greater than 70%.

The reaction in the second step of the second process according to the invention can be conducted with exclusion of air.

The reaction in the second step of the second process according to the invention can be conducted under a protective gas atmosphere, for example under argon or nitrogen, preferably under nitrogen.

The second step of the second process according to the invention can be conducted at standard pressure, elevated pressure or reduced pressure. Preferably, the process according to the invention can be conducted at standard pressure.

Elevated pressure may be a pressure from 1.1 bar to 100 bar, preferably of 1.5 bar to 50 bar, more preferably of 2 bar to 20 bar and very preferably of 2 to 10 bar.

Reduced pressure may be a pressure of 1 mbar to 1000 mbar, preferably 1 mbar to 500 mbar, more preferably 1 mbar to 250 mbar, very preferably 5 mbar to 100 mbar.

The second step of the second process according to the invention can be conducted between 20° C. and 150° C., preferably between 40° C. and 100° C., more preferably between 45° C. and 80° C.

The reaction in the second step of the second process according to the invention can be effected without solvent or in a solvent, for example methanol, ethanol, propanol, butanol, cyclohexanol, N,N-dimethylformamide, dimethyl sulphoxide, pentane, hexane, cyclohexane, heptane, octane, decane, toluene, xylene, acetone, acetonitrile, carbon tetrachloride, chloroform, dichloromethane, 1,2-dichloromethane, tetrachloroethylene, diethyl ether, methyl tert-butyl ether, methyl ethyl ketone, tetrahydrofuran, dioxane, pyridine or ethyl acetate. The solvent may preferably be ethanol.

The reaction in the second step of the second process according to the invention can be conducted without organic solvent. The solvent may be water.

The reaction product in the second step of the second process according to the invention can be filtered, and the filtercake can be washed with an organic solvent. Preferably, an alcohol can be used for washing, more preferably ethanol, or an alkane, more preferably hexane.

The solvent in the second step of the second process according to the invention can subsequently be removed, preferably distilled off.

The reaction product in the second step of the second process according to the invention can be dried after filtration and removal of solvent. The drying can be effected at temperatures of 20° C.-100° C., preferably of 25° C.-50° C. The drying can be effected at a reduced pressure of 1-500 mbar.

The urea-containing silane of the formula I, obtainable in the second step by the second process according to the invention,

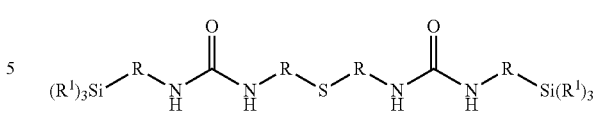

(I)

can be obtained in a yield of greater than 50%, preferably greater than 60%, very preferably greater than 70%.

The product prepared by the second process according to the invention may have a residual content of urea-containing halosilane of the formula V of less than 25 mol %, preferably less than 10 mol %, more preferably less than 5 mol %, very preferably less than 3 mol %.

The relative molar percentages of the urea-containing halosilanes of the formula V in the product prepared by the second process according to the invention are determined in the $^1$H NMR by integration of the hydrogen atoms in the —CH$_2$C$\underline{H}_2$—Cl group of the urea-containing halosilanes of the formula V against the hydrogen atoms in the Si—C$\underline{H}_2$— group of the urea-containing silanes of the formula I.

For the substance of the formula V (EtO)$_3$Si—CH$_2$CH$_2$CH$_2$—NH—CO—NH—CH$_2$CH$_2$—Cl, for example, the integral of the hydrogen atoms of the —CH$_2$C$\underline{H}_2$—Cl group (δ=3.17 ppm) is used for the determination of the relative contents.

The product prepared by the second process according to the invention may have a residual content of isocyanatosilane of the formula VI of less than 10 mol %, preferably less than 5 mol %, more preferably less than 1 mol %, very preferably less than 0.1 mol %.

The relative molar percentages of the isocyanatosilanes of the formula VI in the product within a range of >1 mol %, prepared by the second process according to the invention, are determined in the $^{13}$C NMR by integration of the carbon atoms in the —N$\underline{C}$O group of the isocyanatosilanes of the formula VI against the carbon atoms in the Si—$\underline{C}$H$_2$— group of the urea-containing silanes of the formula I.

For the substance of the formula VI (EtO)$_3$Si—CH$_2$—CH$_2$—CH$_2$—NCO, for example, the integral of the carbon atoms of the —N$\underline{C}$O group (δ=122.22 ppm) is used for the determination of the relative contents within a range of >1 mol %.

The relative molar percentages of the isocyanatosilanes of the formula VI in the product within a range of <1 mol %, prepared by the second process according to the invention, are determined by quantitative FT-IR spectroscopy known to those skilled in the art. The method is calibrated by using calibration solutions of suitable concentration (for example in C$_2$Cl$_4$). For the measurement, about 1 g sample is weighed into a 25 ml rollneck bottle, and 25 g of C$_2$Cl$_4$ are added. The sample is agitated on an agitator for 1-2 hours. Thereafter, the lower liquid phase is metered cautiously into a 20 mm IR cuvette and analysed by FT-IR spectroscopy (4000-1200 cm$^{-1}$, resolution 2 cm$^{-1}$). Under the same conditions, a spectrum of the solvent is recorded for subtraction.

For the substance of the formula VI (EtO)$_3$Si—CH$_2$—CH$_2$—CH$_2$—NCO, for example, the wavelength of the valence vibration of the —NCO group at 2270 cm$^{-1}$ is used for the determination of the relative contents within a range of <1 mol %.

The product prepared by the second process according to the invention may have a residual content of amine of the formula VII of less than 25 mol %, preferably less than 10 mol %, more preferably less than 5 mol %, very preferably less than 3 mol %.

The relative molar percentages of the amines of the formula VII in the product prepared by the second process according to the invention are determined in the $^{13}$C NMR by integration of the carbon atoms in the —$\underline{C}H_2$—$NH_2$ group of the amines of the formula VII against the carbon atoms in the Si—$\underline{C}H_2$— group of the urea-containing silanes of the formula I.

For the substance of the formula VII $H_2N$—$CH_2$—$CH_2$—Cl, for example, the integral of the carbon atoms of the $H_2N$—$\underline{C}H_2$—$CH_2$—Cl group ($\delta$=39.47 ppm) or of the $H_2N$—$CH_2$—$\underline{C}H_2$—Cl group ($\delta$=37.95 ppm) is used for the determination of the relative contents.

The amines of the formula VII can be prepared, prior to the reaction with the isocyanatosilanes of the formula VI, from the hydrochloride salts of the amines of the formula VIII

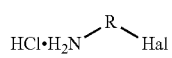
(VIII)

by addition of a base, preferably NaOEt. The base can be added until a pH between 7 and 14 is established.

In a preferred embodiment, the second process for preparing urea-containing silanes of the formula I

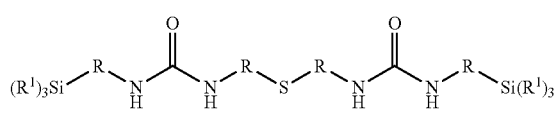
(I)

where R and R1 are each as defined above may be characterized in that the hydrochloride salt of the amine of the formula VIII

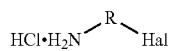
(VIII)

is dissolved in ethanol and reacted with a base,
then the isocyanatosilane of the formula VI

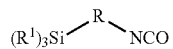
(VI)

is added, then sodium sulphide of the formula IV $Na_2S$    (IV)

is added, the mixture is filtered and the solvent is removed, preferably distilled off.

The product prepared by the second process according to the invention may have a residual content of hydrochloride salt of the amine of the formula VIII of less than 25 mol %, preferably less than 10 mol %, more preferably less than 5 mol %, very preferably less than 3 mol %.

The relative molar percentages of the hydrochloride salt of the amines of the formula VIII in the product prepared by the second process according to the invention are determined in the $^{13}$C NMR by integration of the carbon atoms in the —$\underline{C}H_2$—$NH_2$.HCl group of the hydrochloride salt of the amines of the formula VIII against the carbon atoms in the Si—$\underline{C}H_2$— group of the compounds of the formula I.

For the substance of the formula VIII $HCl.H_2N$—$CH_2$—$CH_2$—Cl, for example, the integral of the carbon atoms of the $HCl.H_2N$—$\underline{C}H_2$—$CH_2$—Cl group ($\delta$=41.25 ppm) or of the $HCl.H_2N$—$CH_2$—$\underline{C}H_2$—Cl group ($\delta$=40.79 ppm) is used for the determination of the relative contents.

Urea-containing silanes of the formula I prepared by the processes according to the invention can be characterized by a $^1$H, $^{13}$C or $^{29}$Si NMR method known to those skilled in the art.

The soluble fraction of the urea-containing silanes of the formula I in the products obtained by the processes according to the invention in DMSO-d$^6$ or CDCl$_3$ is determined by adding an internal standard, for example triphenylphosphine oxide (TPPO), in DMSO-d6 or in CDCl$_3$, and a $^1$H NMR method known to those skilled in the art.

The urea-containing silanes of the formula I can be used as adhesion promoters between inorganic materials, for example glass beads, glass flakes, glass surfaces, glass fibres, or oxidic fillers, preferably silicas such as precipitated silicas and fumed silicas, and organic polymers, for example thermosets, thermoplastics or elastomers, or as crosslinking agents and surface modifiers for oxidic surfaces.

The urea-containing silanes of the formula I may be used as coupling reagents in filled rubber mixtures, examples being tyre treads, industrial rubber articles or footwear soles.

Advantages of the inventive urea-containing silanes of the formula I are improved processing characteristics, wet skid characteristics and dynamic viscosity in rubber mixtures.

EXAMPLES

Comparative Example 1

Preparation of [(EtO)$_3$Si—(CH$_2$)$_3$—NH—C(=O)—NH—(CH$_2$)$_2$—S-]$_2$ in Water An N2-purged 1 l jacketed four-neck flask with precision glass stirrer, reflux condenser, internal thermometer and dropping funnel is initially charged with cystamine dihydrochloride (108.39 g, 0.47 mol, 1.00 eq) which was dissolved in demineralized water (382 ml). By means of a dropping funnel, 50% KOH solution (92.31 g, 0.82 mol, 1.75 eq) is metered in at 15-23° C. and the mixture is stirred for 30 min. Then 3-isocyanatopropyltriethoxysilane (221.05 g, 0.85 mol, 1.8 eq) is metered in at such a rate that an internal temperature of 30° C. is not exceeded. Thereafter, the mixture is stirred at 24° C. for one hour. The white suspension is filtered under pressure, rinsed with three portions of demineralized water (340 ml in total) and dried with dry N$_2$ for 2 h. The filtercake is dried in an N$_2$ stream in a rotary evaporator at 35° C. and 166 mbar for 7 h, at 35° C. and 150 mbar for 10 h and at 35° C. and 100 mbar for 9 h. The [(EtO)$_3$Si—(CH$_2$)$_3$—NH—C(=O)—NH—(CH$_2$)$_2$—S-]$_2$ product is a fine white powder (246.38 g, 90.7% of theory);

$^1$H NMR ($\delta_{ppm}$, 500 MHz, DMSO-d6): 0.52 (4H, t), 1.14 (18H, t), 1.42 (4H, m), 2.74 (4H, m), 2.96 (4H, m), 3.29 (4H, m), 3.74 (12H, q), 6.05 (4H, m);

$^{13}$C NMR ($\delta_{ppm}$, 125 MHz, DMSO-d6): 7.3 (2C), 18.2 (6C), 23.5 (2C), 38.5 (2C), 39.6 (2C), 42.0 (2C), 57.7 (6C) 157.9 (2C).

$^{29}$Si NMR ($\delta_{ppm}$, 100 MHz, DMSO-d6): −45.3 (100% silane);

Soluble fractions in d6-DMSO using TPPO internal standard: 86.0%;

Water content (DIN 51777): 0.7%;
Initial melting point: 97° C.;
Residual isocyanate content: 0.08%

Example 1

Preparation of (EtO)$_3$Si—CH$_2$CH$_2$CH$_2$—NH—CO—NH—CH$_2$CH$_2$—S—CH$_2$CH$_2$—NH—CO—NH—CH$_2$CH$_2$CH$_2$—Si(OEt)$_3$ from (EtO)$_3$Si—CH$_2$CH$_2$CH$_2$—NH$_2$, OCN—CH$_2$CH$_2$—Cl and Na$_2$S (Analogously to First Process According to the Invention)

In a first reaction step, 3-aminopropyltriethoxysilane (73.05 g, 0.33 mol, 1.00 eq) is initially charged in pentane (2.5 l) in a 4 l three-neck flask with precision glass stirrer, internal thermometer, dropping funnel and reflux condenser, and cooled to −78° C. 2-Chloroethyl isocyanate (34.82 g, 0.33 mol, 1.00 eq) is added dropwise at −78 to −70° C. within 4.5 h and then the mixture is warmed to room temperature. The white suspension is filtered, washed with pentane and dried with N$_2$ overnight. The (EtO)$_3$Si—CH$_2$CH$_2$CH$_2$—NH—CO—NH—CH$_2$CH$_2$—Cl intermediate (100.52 g, quantitative) is a white, flaky powder.

In a second reaction step, (EtO)$_3$Si—CH$_2$CH$_2$CH$_2$—NH—CO—NH—CH$_2$CH$_2$—Cl (100.00 g, 0.31 mol, 2.00 eq) is initially charged in ethanol (75 ml) in a 500 ml three-neck flask with stirrer, reflux condenser and internal thermometer. Dry sodium sulphide (Na$_2$S, 14.47 g, 0.18 mol, 1.17 eq) is added and the mixture is heated to reflux. After a reaction time of 4.5 h, the mixture is cooled to room temperature and the suspension is filtered. The filtrate is freed of the solvent on a rotary evaporator and dried under reduced pressure. The (EtO)$_3$Si—CH$_2$CH$_2$CH$_2$—NH—CO—NH—CH$_2$CH$_2$—S—CH$_2$CH$_2$—NH—CO—NH—CH$_2$CH$_2$CH$_2$—Si(OEt)$_3$ product (93.34 g, 99.2% of theory) is obtained as a waxy, light green solid.

$^1$H NMR ($\delta_{ppm}$, 500 MHz, CDCl$_3$): 0.64 (4H, t), 1.22 (18H, t), 1.60 (4H, m), 2.66 (4H, t), 3.15 (4H, m), 3.39 (4H, m), 3.82 (12H, q), 5.2-6.4 (4H, br);
$^{13}$C NMR ($\delta_{ppm}$, 125 MHz, CDCl$_3$): 7.8 (2C), 18.3 (6C), 23.8 (2C), 32.8 (2C), 40.2 (2C), 42.8 (2C), 58.4 (6C), 159.2 (2C).

Example 2

Preparation of (EtO)$_3$Si—CH$_2$CH$_2$CH$_2$—NH—CO—NH—CH$_2$CH$_2$—S—CH$_2$CH$_2$—NH—CO—NH—CH$_2$CH$_2$CH$_2$—Si(OEt)$_3$ from (EtO)$_3$Si—CH$_2$CH$_2$CH$_2$—NH$_2$, OCN—CH$_2$CH$_2$—Cl and Na$_2$S (Analogously to the First Process According to the Invention)

In a first reaction step, 3-aminopropyltriethoxysilane (159.39 g, 0.72 mol, 1.00 eq) is initially charged in ethanol (3.0 l) in a 4 l three-neck flask with precision glass stirrer, internal thermometer, dropping funnel and reflux condenser, and cooled to −78° C. 2-Chloroethyl isocyanate (75.92 g, 0.72 mol, 1.00 eq) is added dropwise at −78 to −69° C. within 2.25 h and then the mixture is heated to 50° C. Dry sodium sulphide (Na$_2$S, 28.09 g, 0.36 mol, 0.50 eq) is added in five portions and the mixture is heated to reflux. After a reaction time of 4.5 h, the mixture is cooled to room temperature and the suspension is filtered. The filtrate is freed of the solvent on a rotary evaporator and dried under reduced pressure. The (EtO)$_3$Si—CH$_2$CH$_2$CH$_2$—NH—CO—NH—CH$_2$CH$_2$—S—CH$_2$CH$_2$—NH—CO—NH—CH$_2$CH$_2$CH$_2$—Si(OEt)$_3$ product (214.09 g, 96.7% of theory) is obtained as a waxy, white solid.

$^1$H NMR ($\delta_{ppm}$, 500 MHz, CDCl$_3$): 0.64 (4H, t), 1.22 (18H, t), 1.61 (4H, m), 2.67 (4H, t), 3.15 (4H, m), 3.40 (4H, m), 3.82 (12H, q), 5.16 (2H, br), 5.43 (2H, br);
$^{13}$C NMR ($\delta_{ppm}$, 125 MHz, CDCl$_3$): 7.8 (2C), 18.3 (6C), 23.8 (2C), 33.0 (2C), 40.3 (2C), 42.9 (2C), 58.4 (6C), 159.3 (2C).

Example 3

Preparation of (EtO)$_3$Si—CH$_2$CH$_2$CH$_2$—NH—CO—NH—CH$_2$CH$_2$—S—CH$_2$CH$_2$—NH—CO—NH—CH$_2$CH$_2$CH$_2$—Si(OEt)$_3$ from (EtO)$_3$Si—CH$_2$CH$_2$CH$_2$—NCO, HCl.H$_2$N—CH$_2$CH$_2$—Cl and Na$_2$S (Analogously to the Second Process According to the Invention)

In a first reaction step, 3-chloroethylamine hydrochloride (73.86 g, 0.70 mol, 1.00 eq) is initially charged in ethanol (3.0 l) in a 4 l three-neck flask with precision glass stirrer, internal thermometer, dropping funnel and reflux condenser, and cooled to −78° C., and sodium ethoxide (226.83 g, 0.70 mol, 1.00 eq, 21% in ethanol) is added. 3-Isocyanatopropyl(triethoxysilane) (173.15 g, 0.70 mol, 1.00 eq) is then added dropwise at −78 to −70° C. within 3 h and then the mixture is heated to 50° C. Dry sodium sulphide (Na$_2$S, 27.31 g, 0.35 mol, 0.50 eq) is added in five portions and the mixture is heated to reflux. After a reaction time of 4 h, the mixture is cooled to room temperature and the suspension is filtered. The filtrate is freed of the solvent on a rotary evaporator and dried under reduced pressure. The (EtO)$_3$Si—CH$_2$CH$_2$CH$_2$—NH—CO—NH—CH$_2$CH$_2$—S—CH$_2$CH$_2$—NH—CO—NH—CH$_2$CH$_2$CH$_2$—Si(OEt)$_3$ product (212.68 g, 98.8% of theory) is obtained as a yellow oil.

Example 4

Rubber Mixtures

The formulation used for the rubber mixtures is specified in Table 1 below. In this table, the unit phr means parts by weight based on 100 parts by weight of the raw rubber used. The inventive silane is used in an isomolar proportion in relation to the comparative silane.

TABLE 1

| Substance | Amount [phr] Ref. rubber mixture I cont. Comp. Ex. 1 | Amount [phr] Ref. rubber mixture II cont. Inv. Ex. 2 |
|---|---|---|
| 1st stage | | |
| NR TSR$^a$ | 10 | 10 |
| BR$^b$ | 18 | 18 |
| SSBR$^c$ | 72 | 72 |
| Silica$^d$ | 95 | 95 |
| ZnO | 2.5 | 2.5 |
| Stearic acid | 2.5 | 2.5 |
| TDAE oil | 50 | 50 |
| Antiozonant wax | 2 | 2 |
| 6PPD$^e$ | 2 | 2 |
| Comp. Ex. 1 | 12.1 | — |
| Example 2 | — | 11.5 |
| 2nd stage | | |
| Batch | | |

TABLE 1-continued

| Substance | Amount [phr] Ref. rubber mixture I cont. Comp. Ex. 1 | Amount [phr] Ref. rubber mixture II cont. Inv. Ex. 2 |
|---|---|---|
| Stage 2 | | |
| DPG† | 2 | 2 |
| CBS<sup>g</sup> | 2 | 2 |
| Sulphur | 2 | 2 |

Substances Used:
NR TSR: SIR 20 SED, from Aneka Bumi Pratama (TSR=Technically Specified Rubber; SIR=Standard Indonesian Rubber)
BR: polybutadiene, Europrene Neocis BR 40, from Polimeri
SSBR: Sprintan® SLR-4601, from Styron
silica: ULTRASIL® VN3 GR, from Evonik Industries AG
6PPD: N-(1,3-dimethylbutyl)-N'-phenyl-p-phenylenediamine
DPG: diphenylguanidine
CBS: N-cyclohexyl-2-benzothiazolesulphenamide The mixture was produced under customary conditions in two stages in a laboratory kneader for production of rubber mixtures (volume 300 milliliters to 3 liters), by first mixing, in the first mixing stage (base mixing stage), all the constituents apart from the vulcanization system (sulphur and vulcanization-influencing substances) at 145 to 165° C., target temperatures of 152 to 157° C., for 200 to 600 seconds. Addition of the vulcanization system in the second stage (ready-mix stage) produces the finished mixture, with mixing at 90 to 120° C. for 180 to 300 seconds.

The general process for producing rubber mixtures and vulcanizates thereof is described in "Rubber Technology Handbook", W. Hofmann, Hanser Verlag 1994.

The rubber testing is effected by the test methods specified in Table 2

TABLE 2

| Physical testing | Standard/conditions |
|---|---|
| Moving die rheometer (rotorless vulcameter): | ISO 6502 |
| Minimum torque (dNm) | ASTM D5289-12 |
| Rebound resilience at 23° C. (%) | DIN 53512 |
| Dynamic/mechanical analysis at 55° C. | ISO 4664-1 |
| Dynamic storage Modulus E' at 0.15% elongation and at 8% elongation (MPa) | |

The mixtures are used to produce test specimens by vulcanization under pressure at 160° C. after $t_{95}$ (measured on a moving die rheometer to ISO 6502/ASTM D5289-12). Table 3 reports the rubber data.

TABLE 3

| Substance | Ref. rubber mixture I cont. Comp. Ex. 1 | Ref. rubber mixture II cont. Inv. Ex. 2 |
|---|---|---|
| Raw mixture results: | | |
| Moving die method: minimum torque after 3<sup>rd</sup> stage [dNm] | 4.5 | 4.1 |
| Vulcanizate results: | | |
| Rebound resilience 23° C. [%] | 25.7 | 21.8 |
| Dynamic/mechanical analysis at 55° C. E' at 0.15% elongation (MPa) | 13.3 | 21.6 |

TABLE 3-continued

| Substance | Ref. rubber mixture I cont. Comp. Ex. 1 | Ref. rubber mixture II cont. Inv. Ex. 2 |
|---|---|---|
| Dynamic/mechanical analysis at 55° C. E' at 8% elongation (MPa) | 6.6 | 5.5 |
| Dynamic/mechanical analysis at 55° C. E' at 8% extension - E' at 0.15% extension (MPa) | 6.7 | 16.1 |

Rubber mixtures II containing the inventive urea-containing silane from Example 2 shows improved processing characteristics (low minimum torque after the 3<sup>rd</sup> mixing stage), improved wet skid characteristics (rebound resilience at 23° C.) and increased dynamic viscosity (E' at 0.15% extension and E' at 8% elongation-E' at 0.15% elongation compared to reference rubber mixture I containing the Comparative Example 1 (disulphide silane) with isomolar usage.

What is claimed is:

1. A urea-containing silane of formula I

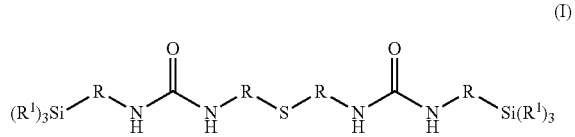

where each $R^1$ is independently selected from the group consisting of a C1-C10 alkoxy group, a C2-C10 cyclic dialkoxy group, a phenoxy group, a C4-C10 cycloalkoxy group, a C6-C20 aryl group, a C1-C10 alkyl group, a C2-C20 alkenyl group, a C7-C20 aralkyl group or a halogen, and each R is independently a branched or unbranched, saturated or unsaturated, aliphatic, aromatic or mixed aliphatic/aromatic divalent C1-C30 hydrocarbon group.

2. The urea-containing silane according to claim 1 wherein the urea-containing silane is
((EtO)₃Si—CH₂—NH—CO—NH—CH₂)₂S,
((EtO)₃Si—CH₂CH₂—NH—CO—NH—CH₂)₂S,
((EtO)₃Si—CH₂—NH—CO—NH—CH₂CH₂)₂S,
((EtO)₃Si—CH₂CH₂—NH—CO—NH—CH₂CH₂)₂S,
((EtO)₃Si—CH₂CH₂CH₂—NH—CO—NH—CH₂)₂S,
((EtO)₃Si—CH₂CH₂CH₂—NH—CO—NH—CH₂CH₂)₂S,
((EtO)₃Si—CH₂—NH—CO—NH—CH₂CH₂CH₂)₂S,
((EtO)₃Si—CH₂CH₂—NH—CO—NH—CH₂CH₂CH₂)₂S,
((EtO)₃Si—CH₂CH₂CH₂—NH—CO—NH—CH₂CH₂CH₂)₂S,
((MeO)₃Si—CH₂—NH—CO—NH—CH₂)₂S,
((MeO)₃Si—CH₂CH₂—NH—CO—NH—CH₂)₂S,
((MeO)₃Si—CH₂—NH—CO—NH—CH₂CH₂)₂S,
((MeO)₃Si—CH₂CH₂—NH—CO—NH—CH₂CH₂)₂S,
((MeO)₃Si—CH₂CH₂CH₂—NH—CO—NH—CH₂)₂S,
((MeO)₃Si—CH₂CH₂CH₂—NH—CO—NH—CH₂CH₂)₂S,
((MeO)₃Si—CH₂—NH—CO—NH—CH₂CH₂CH₂)₂S,
((MeO)₃Si—CH₂CH₂—NH—CO—NH—CH₂CH₂CH₂)₂S or
((MeO)₃Si—CH₂CH₂CH₂—NH—CO—NH—CH₂CH₂CH₂)₂S.

3. The urea-containing silane according to claim 1, wherein the urea-containing silane is (EtO)₃Si—CH₂CH₂CH₂—NH—CO—NH—CH₂CH₂—S—CH₂CH₂—NH—CO—NH—CH₂CH₂CH₂—Si(OEt)₃.

4. A process for preparing the urea-containing silane of claim 1, wherein, in a first step, an aminosilane of formula II

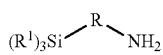   (II)

is reacted with an isocyanate of formula III

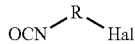   (III)

where R and R¹ are each as defined in claim 1 and Hal is F, Cl, Br or I, and, in a second step, the product from the first step is reacted with a sodium sulphide of formula (IV)

Na₂S   (IV).

5. The process of claim 4, wherein the first step is conducted under a protective gas atmosphere.

6. The process of claim 4, wherein the second step is conducted under a protective gas atmosphere.

7. The process of claim 4, wherein the first step is conducted at temperatures between −78° C. and 100° C.

8. The process of claim 4, wherein the second step is conducted at temperatures between 20° C. and 150° C.

9. The process of claim 4, wherein ethanol is used as solvent in the first step.

10. The process of claim 4, wherein ethanol is used as solvent in the second step.

11. The process of claim 9, wherein the ethanol is distilled off after the first step.

12. The process of claim 10, wherein the ethanol is distilled off after the second step.

13. A process of for preparing the urea-containing silane of claim 1, wherein, in a first step, an isocyanatosilane of formula VI

   (VI)

is reacted with an amine of formula VII

   (VII)

where R and R¹ are each as defined in claim 1 and Hal is F, Cl, Br or I, and, in a second step, the product from the first step is reacted with sodium sulphide of the formula (IV)

Na₂S   (IV).

14. The process of claim 13, wherein the amine of formula VII, prior to reaction with the isocyanatosilane of formula VI, is prepared from a hydrochloride salt of a diamine of formula VIII Cl⁻⁺H₃N—R—S—S—R—NH₃⁺Cl⁻   (VIII)

by addition of a base.

15. The process of claim 14, wherein the base is NaOEt.

16. The process of claim 13, wherein the product is dried.

* * * * *